(12) United States Patent
Koshino

(10) Patent No.: US 12,383,232 B2
(45) Date of Patent: Aug. 12, 2025

(54) ULTRASOUND SYSTEM AND CONTROL METHOD OF ULTRASOUND SYSTEM

(71) Applicant: FUJIFILM Corporation, Tokyo (JP)

(72) Inventor: Riko Koshino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 295 days.

(21) Appl. No.: 18/176,142

(22) Filed: Feb. 28, 2023

(65) Prior Publication Data

US 2023/0200783 A1 Jun. 29, 2023

Related U.S. Application Data

(63) Continuation of application No. PCT/JP2021/028555, filed on Aug. 2, 2021.

(30) Foreign Application Priority Data

Sep. 23, 2020 (JP) .................................. 2020-158336

(51) Int. Cl.
*A61B 8/00* (2006.01)
*A61B 8/08* (2006.01)

(52) U.S. Cl.
CPC ............ *A61B 8/463* (2013.01); *A61B 8/0825* (2013.01); *A61B 8/469* (2013.01); *A61B 8/5261* (2013.01)

(58) Field of Classification Search
CPC ......... A61B 8/461; A61B 8/463; A61B 8/469; A61B 8/5261; A61B 6/5247
See application file for complete search history.

(56) References Cited

U.S. PATENT DOCUMENTS

| | | |
|---|---|---|
| 2006/0004278 A1 | 1/2006 | Giger et al. |
| 2007/0274585 A1 | 11/2007 | Zhang et al. |
| 2009/0240150 A1 | 9/2009 | Wang et al. |
| 2012/0014578 A1 | 1/2012 | Karssemeijer et al. |
| 2012/0184852 A1 | 7/2012 | Arai et al. |
| 2015/0146855 A1 | 5/2015 | Futamura |
| 2021/0052247 A1 | 2/2021 | Kobayashi |

FOREIGN PATENT DOCUMENTS

| | | |
|---|---|---|
| JP | 2003-000575 A | 1/2003 |
| JP | 2006-146863 A | 6/2006 |
| JP | 2006-167267 A | 6/2006 |
| JP | 2013-123528 A | 6/2013 |
| JP | 2014-039877 A | 3/2014 |
| JP | 2015-100661 A | 6/2015 |
| JP | 2019-193788 A | 11/2019 |

OTHER PUBLICATIONS

International Search Report issued in PCT/JP2021/028555; mailed Oct. 5, 2021.

(Continued)

*Primary Examiner* — Carolyn A Pehlke
(74) *Attorney, Agent, or Firm* — Studebaker Brackett PLLC

(57) ABSTRACT

In an ultrasound system and a control method of the ultrasound system, a second region-of-interest specifying unit specifies a second region of interest included in an ultrasound image, and an identity determination unit determines whether or not a first region of interest included in a radiation image and the second region of interest are identical to each other.

21 Claims, 7 Drawing Sheets

(56) References Cited

OTHER PUBLICATIONS

International Preliminary Report on Patentability and Written Opinion issued in PCT/JP2021/028555; issued Mar. 28, 2023.

An Office Action; "Notice of Reasons for Refusal," mailed by the Japanese Patent Office on Mar. 26, 2024, which Corresponds to Japanese Patent Application No. 2022-551173 and is related to U.S. Appl. No. 18/176,142; with English language translation.

The extended European search report issued by the European Patent Office on Feb. 26, 2024, which corresponds to European Patent Application No. 21871983.9-1126 and is related to U.S. Appl. No. 18/176,142.

An Office Action; "Notice of Reasons for Refusal," mailed by the Japanese Patent Office on May 27, 2025, which corresponds to Japanese Patent Application No. 2024-144105 and is related to U.S. Appl. No. 18/176,142; with English language translation.

ULTRASOUND SYSTEM AND CONTROL METHOD OF ULTRASOUND SYSTEM

CROSS-REFERENCE TO RELATED APPLICATIONS

This application is a Continuation of PCT International Application No. PCT/JP2021/028555 filed on Aug. 2, 2021, which claims priority under 35 U.S.C. § 119(a) to Japanese Patent Application No. 2020-158336 filed on Sep. 23, 2020. The above applications are hereby expressly incorporated by reference, in its entirety, into the present application.

BACKGROUND OF THE INVENTION

1. Field of the Invention

The present invention relates to an ultrasound system and a control method of the ultrasound system which have a function of determining whether or not a region of interest of a breast included in a radiation image and a region of interest of a breast included in an ultrasound image are identical to each other.

2. Description of the Related Art

In a case where a region of interest of a breast with a possibility of being a lesion part is found by the mammography examination, in some cases, by ultrasonography, a region of interest of a breast in an ultrasound image, which corresponds to the region of interest of the breast in a mammography image is specified, and a qualitative diagnosis is performed to determine whether the region of interest of the breast included in the ultrasound image is a lesion part.

Here, there are JP2006-146863A and JP2013-123528A as the documents in the related art that are references for the present invention.

In a treatment system of JP2006-146863A, three-dimensional volume data of multi-slice images is acquired using an image diagnostic apparatus such as an X-ray computed tomography (CT) device and a magnetic resonance imaging (MRI) device, and a treatment site is set and marked on the volume data. A position sensor that detects three-dimensional position and inclination of an ultrasound probe is attached to a treatment probe, and information for understanding where the ultrasound probe is positioned on a subject is obtained. From the volume data of the image diagnostic apparatus, tomographic image data of the same cross section as the ultrasound image according to the position of the treatment probe is extracted to be used as a reference image, and the marked treatment site is displayed on the reference image in a superimposed manner. Then, the reference image and the ultrasound image are displayed on the monitor in real time, and in a case where the marked treatment site appears on the reference image, the treatment probe is held at the position to execute a treatment.

JP2013-123528A relates to an image diagnosis support device that assists in diagnosing a subject using a plurality of images obtained by imaging the same subject. In the image diagnosis support device, the position of a lesion on the image is used to calculate a vector from a reference point on the image to the lesion for each lesion on the plurality of images. A similarity degree between vectors on the plurality of images is calculated. As a result, the lesion corresponding to each vector is determined to be the same lesion in a case where the similarity degree is equal to or greater than a predetermined threshold value, and the lesion corresponding to each vector is determined to be a different lesion in a case where the similarity degree is less than the threshold value.

SUMMARY OF THE INVENTION

The posture of the subject during the examination differs between a mammography examination and ultrasonography due to the difference in the examination method. For example, in the mammography examination, a mammography image of a breast is generated in a state where the breast of the subject in an upright position is pressed by a compression plate. On the other hand, in the ultrasonography, an ultrasound image of the breast of the subject in a supine state is generated. Therefore, the shape and size of a region of interest of the breast included in the mammography image and a region of interest of the breast included in the ultrasound image appear different, and in the ultrasonography, there is a problem in that it is difficult to specify the region of interest of the breast in the ultrasound image, which corresponds to the region of interest of the breast in the mammography image.

An object of the present invention is to provide an ultrasound system and a control method of the ultrasound system which can determine whether or not a region of interest of a breast included in a radiation image and a region of interest of a breast included in an ultrasound image are identical to each other.

In order to achieve the object, an aspect of the present invention provides an ultrasound system including an ultrasound probe; an image generation unit that generates, from a reception signal obtained by performing transmission and reception of an ultrasound beam with respect to a breast of a subject by using the ultrasound probe, an ultrasound image including a second region of interest of the breast of the subject corresponding to a first region of interest of the breast of the subject included in a radiation image; a second region-of-interest specifying unit that specifies the second region of interest included in the ultrasound image; and an identity determination unit that determines whether or not the first region of interest included in the radiation image and the second region of interest are identical to each other.

It is preferable that the ultrasound system further includes an ultrasound diagnostic apparatus, and the ultrasound diagnostic apparatus includes the ultrasound probe, the image generation unit, the second region-of-interest specifying unit, and the identity determination unit.

It is preferable that the ultrasound system further includes an ultrasound diagnostic apparatus; and a remote computer connected to the ultrasound diagnostic apparatus via a network, the ultrasound diagnostic apparatus includes the ultrasound probe and the image generation unit, and the remote computer includes the identity determination unit.

It is preferable that the ultrasound diagnostic apparatus includes a monitor and a display control unit, and the display control unit displays the radiation image and the ultrasound image side by side on the monitor.

It is preferable that the remote computer is a workstation, and includes a monitor and a display control unit, and the display control unit displays the radiation image and the ultrasound image side by side on the monitor.

It is preferable that the remote computer is a workstation, the workstation includes a client connected via the network, the client includes a monitor and a display control unit, and the display control unit displays the radiation image and the ultrasound image side by side on the monitor.

It is preferable that the remote computer is a picture archiving and communication system, the picture archiving and communication system includes a monitor and a display control unit, and the display control unit displays the radiation image and the ultrasound image side by side on the monitor.

It is preferable that the display control unit enlarges and displays each of the first region of interest included in the radiation image and the second region of interest included in the ultrasound image on the monitor.

It is preferable that the display control unit displays a result of determination by the identity determination unit on the monitor.

It is preferable that the identity determination unit performs determination on the basis of a radiation image in one direction, the radiation image including the first region of interest, or radiation images in two directions different from each other, the radiation images including the first region of interest.

It is preferable that the identity determination unit performs determination on the basis of an ultrasound image of one cross section, the ultrasound image including the second region of interest, or ultrasound images of two cross sections orthogonal to each other, the ultrasound images including the second region of interest.

It is preferable that the identity determination unit performs determination on the basis of volume data consisting of ultrasound images of a plurality of cross sections different from each other, the ultrasound images including the second region of interest, or a three-dimensional image reconstructed using the volume data.

It is preferable that the ultrasound system further includes an input device that receives an instruction input from a user, and the identity determination unit specifies the second region of interest included in the ultrasound image on the basis of an instruction to designate the second region of interest, input from the user.

It is preferable that the second region-of-interest specifying unit has a first determination model that has learned, using learning ultrasound images of the breast of the subject as first teacher data, a relationship between the learning ultrasound image and a region of interest included in the learning ultrasound image for a plurality of pieces of the first teacher data, and the first determination model uses the ultrasound image as an input, and specifies the second region of interest included in the ultrasound image.

It is preferable that the ultrasound image is a video, and the first determination model uses the video as an input, and specifies the second region of interest included in the video.

It is preferable that the identity determination unit has a second determination model that has learned, using learning radiation images including a region of interest of the breast of the subject and the learning ultrasound images including the same region of interest of the breast of the subject as the region of interest included in the learning radiation image as one set of second teacher data, a relationship between the learning radiation image and the learning ultrasound image, and whether or not the region of interest included in the learning radiation image and the region of interest included in the learning ultrasound image are identical to each other, for a plurality of pieces of the second teacher data, and the second determination model uses one set of the radiation image and the ultrasound image as an input, and outputs a result of determination on whether or not the first region of interest included in the radiation image and the second region of interest included in the ultrasound image are identical to each other.

It is preferable that the ultrasound system further includes an input device that receives an instruction input from a user, and the identity determination unit starts determination on the basis of a determination start instruction input from the user.

It is preferable that the ultrasound system further includes an input device that receives an instruction input from a user, and the identity determination unit starts determination on the basis of an instruction of a freeze operation for the ultrasound image input from the user.

It is preferable that the identity determination unit starts determination on the basis of an instruction to designate the second region of interest input from the user after the ultrasound image is generated on the basis of the instruction of the freeze operation for the ultrasound image input from the user.

It is preferable that the identity determination unit starts determination in a case where it is specified that a plurality of the first regions of interest are included in the radiation image or a plurality of the second regions of interest are included in the ultrasound image.

It is preferable that the identity determination unit specifies the second region of interest included in the ultrasound image on the basis of information on the first region of interest in the radiation image acquired from outside.

Another aspect of the present invention provides a control method of an ultrasound system, the control method including generating, from a reception signal obtained by performing transmission and reception of an ultrasound beam with respect to a breast of a subject by using an ultrasound probe, an ultrasound image including a second region of interest of the breast of the subject corresponding to a first region of interest of the breast of the subject included in a radiation image; specifying the second region of interest included in the ultrasound image; and determining whether or not the first region of interest included in the radiation image and the second region of interest are identical to each other.

According to the present invention, the second region of interest of the breast included in the ultrasound image can be specified, and the determination on whether or not the first region of interest of the breast included in the radiation image and the second region of interest are identical to each other can be automatically performed. Therefore, the user does not confuse the first region of interest of the breast included in the radiation image with the second region of interest of the breast included in the ultrasound image.

DESCRIPTION OF THE PREFERRED EMBODIMENTS

Hereinafter, an ultrasound system and a control method of the ultrasound system according to the present invention will be described in detail on the basis of preferred embodiments illustrated in the accompanying drawings.

Figure 1:
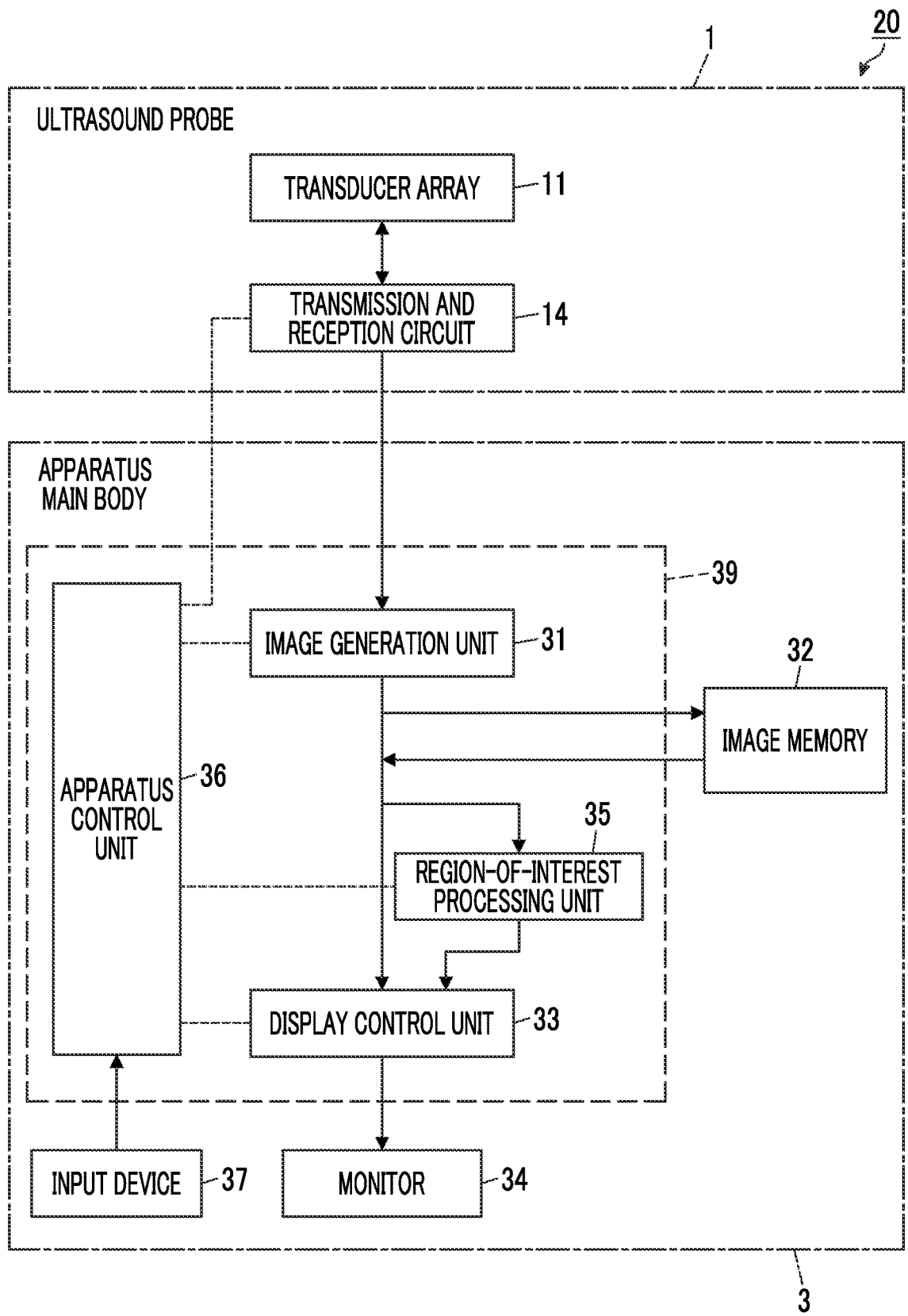
FIG. 1 is a block diagram of an embodiment illustrating a configuration of an ultrasound system of the present invention.
Figure 2:
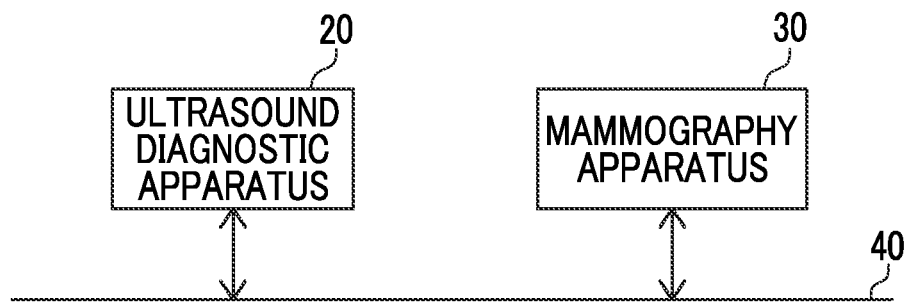
FIG. 2 is a block diagram of an embodiment illustrating a configuration in a case where an ultrasound diagnostic apparatus acquires a mammography image from a mammography apparatus.

FIG. 1 is a block diagram of an embodiment illustrating a configuration of an ultrasound system of the present invention. The ultrasound system illustrated in FIG. 1 includes an ultrasound diagnostic apparatus 20 including an ultrasound probe 1 and an apparatus main body 3 connected to the ultrasound probe 1. As illustrated in FIG. 2, the ultrasound diagnostic apparatus 20 is connected to a mammography apparatus 30 via, for example, a network 40 such as a local network in a hospital, and thereby data can be bidirectionally delivered.

The ultrasound probe 1 scans a subject using an ultrasound beam, and outputs a sound ray signal corresponding to an ultrasound image. As illustrated in FIG. 1, the ultrasound probe 1 includes a transducer array 11 and a transmission and reception circuit 14. The transducer array 11 and the transmission and reception circuit 14 are bidirectionally connected to each other. Further, an apparatus control unit 36 to be described later is connected to the transmission and reception circuit 14.

The transducer array 11 has a plurality of ultrasonic transducers arranged in a one-dimensional or two-dimensional manner. According to a drive signal supplied from the transmission and reception circuit 14, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 3:
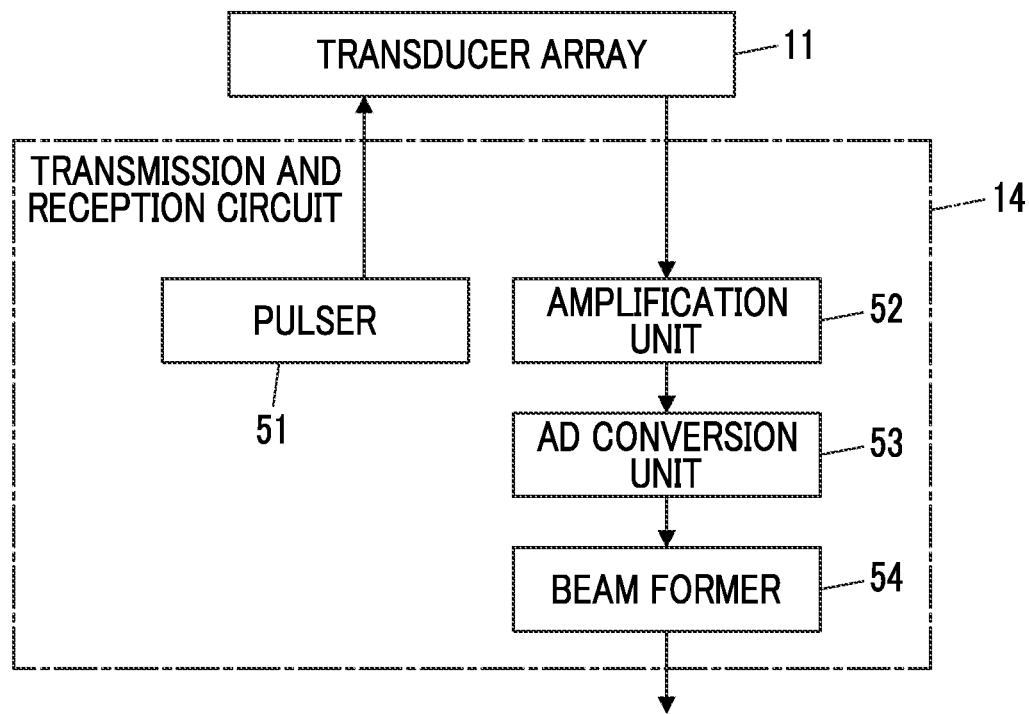
FIG. 3 is a block diagram of an embodiment illustrating a configuration of a transmission and reception circuit.

The transmission and reception circuit 14 causes the transducer array 11 to transmit the ultrasonic wave, and performs reception focusing processing on the reception signal output from the transducer array 11 that has received the ultrasound echo to generate a sound ray signal, under the control of the apparatus control unit 36. As illustrated in FIG. 3, the transmission and reception circuit 14 has a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of transducers of the transducer array 11 form an ultrasound beam on the basis of a transmission delay pattern selected by the apparatus control unit 36, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 52.

The amplification unit 52 amplifies the signals input from each transducer constituting the transducer array 11, and transmits the amplified signals to the AD conversion unit 53. The AD conversion unit 53 converts the analog signal transmitted from the amplification unit 52 into digital reception data, and outputs the reception data to the beam former 54.

The beam former 54 performs so-called reception focusing processing in which addition is performed by giving delays to respective pieces of the reception data converted by the AD conversion unit 53 according to a sound speed distribution or a sound speed set on the basis of a reception delay pattern selected by the apparatus control unit 36. Through the reception focusing processing, a sound ray signal in which each piece of the reception data converted by the AD conversion unit 53 is phased and added and the focus of the ultrasound echo is narrowed is generated.

Next, the apparatus main body 3 displays the ultrasound image on the basis of the sound ray signal generated by the ultrasound probe 1. As illustrated in FIG. 1, the apparatus main body 3 includes an image generation unit 31, an image memory 32, a region-of-interest processing unit 35, a display control unit 33, the apparatus control unit 36, a monitor (display unit) 34, and an input device 37.

The display control unit 33 and the monitor 34 are sequentially connected in series to the image generation unit 31. Each of the image memory 32 and the region-of-interest processing unit 35 is connected to the image generation unit 31, and the display control unit 33 is connected to the image memory 32 and the region-of-interest processing unit 35. The apparatus control unit 36 is connected to the transmission and reception circuit 14, the image generation unit 31, the display control unit 33, and the region-of-interest processing unit 35, and the input device 37 is connected to the apparatus control unit 36.

Figure 4:
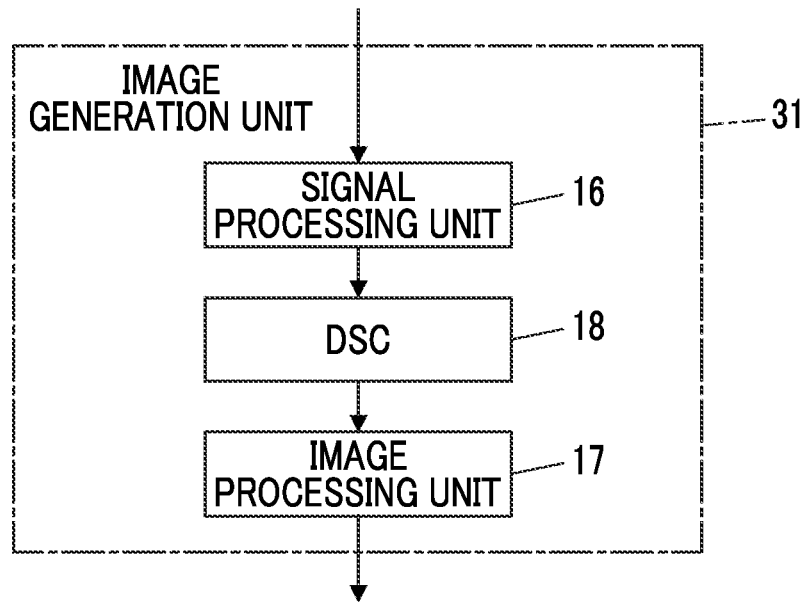
FIG. 4 is a block diagram of an embodiment illustrating a configuration of an image generation unit.

The image generation unit 31 generates the ultrasound image (ultrasound image signal) on the basis of the sound ray signal generated by the transmission and reception circuit 14 under the control of the apparatus control unit 36. As illustrated in FIG. 4, the image generation unit 31 has a configuration in which a signal processing unit 16, a digital scan converter (DSC) 18, and an image processing unit 17 are sequentially connected in series.

The signal processing unit 16 generates image information data corresponding to the ultrasound image on the basis of the sound ray signal generated by the transmission and reception circuit 14. More specifically, the signal processing unit 16 generates the image information data representing tomographic image information regarding tissues inside the subject, by performing envelope detection processing after signal processing, for example, correcting the attenuation of the sound ray signal generated by the beam former 54 of the transmission and reception circuit 14, which is caused by the propagation distance according to the depth of the reflection position of the ultrasonic wave.

The DSC 18 raster-converts the image information data generated by the signal processing unit 16 into an image signal according to a normal television signal scanning method.

The image processing unit 17 performs various kinds of image processing such as brightness correction, gradation correction, sharpness correction, image size correction, refresh rate correction, scanning frequency correction, and color correction according to a display format of the monitor 34, on the image signal input from the DSC 18 to generate the ultrasound image (ultrasound image signal), and then outputs the generated ultrasound image to the display control unit 33 and the image memory 32.

In the present embodiment, the image generation unit 31 generates an ultrasound image including a second region of interest of the breast of the subject corresponding to a first region of interest of the breast of the subject included in the radiation image from the reception signal obtained by performing transmission and reception of the ultrasound beams with respect to the breast of the subject using the ultrasound probe 1 (more precisely, transducer array 11), in other words, from the sound ray signal generated from the reception signal by the transmission and reception circuit 14.

The image memory 32 is a memory that stores ultrasound images (ultrasound image signal) of the series of a plurality of frames, which are generated for each diagnosis by the image generation unit 31. Here, as the image memory 32, recording media such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

Figure 5:
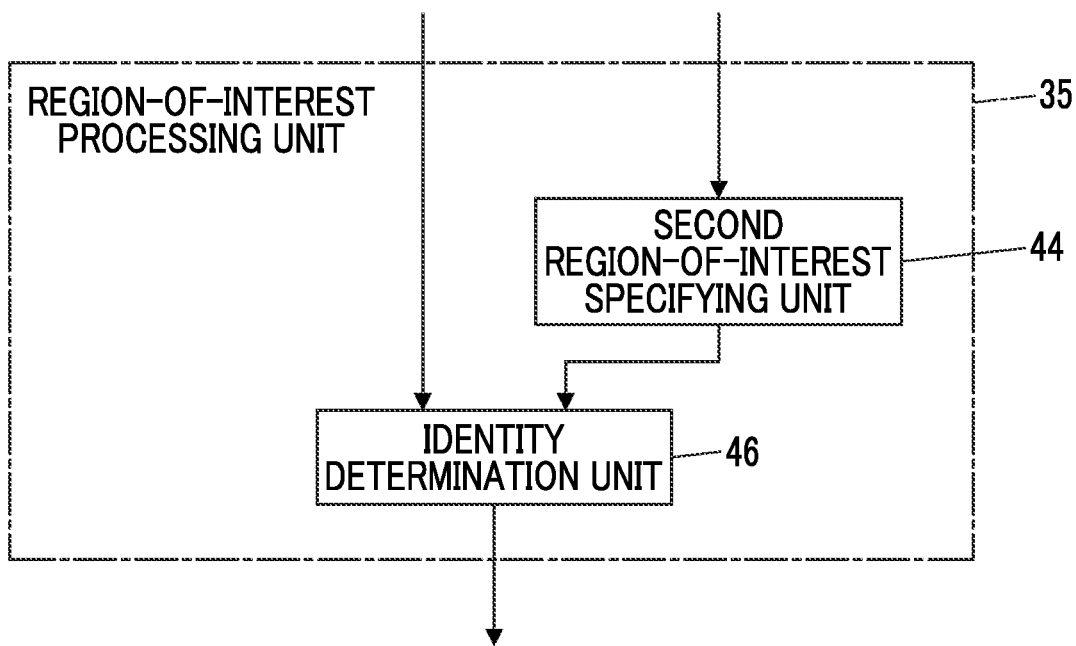
FIG. 5 is a block diagram of an embodiment illustrating a configuration of a region-of-interest processing unit.

The region-of-interest processing unit 35 performs processing of specification of the second region of interest and identity determination between the first region of interest and the second region of interest on the first region of interest of the breast of the subject included in the mammography image and the second region of interest of the breast of the subject included in the ultrasound image, under the control of the apparatus control unit 36. As illustrated in FIG. 5, the region-of-interest processing unit 35 includes a second region-of-interest specifying unit 44 and an identity determination unit 46.

The second region-of-interest specifying unit 44 has a first determination model, and specifies the second region of interest of the breast of the subject included in the ultrasound image using the first determination model.

The first determination model is a trained model that has learned, using learning ultrasound images of the breast of any subject as first teacher data, a relationship between the learning ultrasound image and a region of interest of the breast included in the learning ultrasound image, for a plurality of pieces of the first teacher data.

The first determination model uses an ultrasound image that is a determination target as an input, and outputs a determination result (prediction result) of the second region of interest of the breast included in the ultrasound image on the basis of the training result. That is, the second region of interest of the breast included in the ultrasound image is specified by the first determination model.

The first determination model may learn normal data of the breast (data with no region of interest) as the first teacher data, and may output a determination result indicating being abnormal, that is, there is a second region of interest in a case where abnormal data (data with a region of interest) is input. Alternatively, the first determination model may learn abnormal data of the breast as the first teacher data, and may output a determination result indicating being normal, that is, there is no second region of interest in a case where normal data is input. The determination result may be output together with the coordinates and position of the extracted second region of interest.

It is not essential that the second region-of-interest specifying unit 44 has the first determination model, and may specify the second region of interest of the breast included in the ultrasound image on the basis of an instruction to enclose the second region of interest of the breast with a rectangular frame line, which is input from the user, for example. Further, an image analysis unit that analyzes the ultrasound image may be provided, and the second region-of-interest specifying unit 44 may specify the second region of interest of the breast included in the ultrasound image on the basis of an analysis result of the ultrasound image by the image analysis unit.

The identity determination unit 46 has a second determination model, determines whether or not the first region of interest of the breast included in the mammography image and the second region of interest of the breast included in the ultrasound image are identical to each other using the second determination model, and outputs the determination result.

The second determination model is a trained model that has learned, using learning mammography images including a region of interest of the breast of any subject and learning ultrasound images including the same region of interest of the breast of the subject as the region of interest of the breast included in the learning mammography image as one set of second teacher data, a relationship between the learning mammography image and the learning ultrasound image, and whether or not the region of interest of the breast included in the learning mammography image and the region of interest of the breast included in the learning ultrasound image are identical to each other, for a plurality of pieces of second teacher data.

The learning mammography image and the learning ultrasound image may be images including only the region of interest of the breast.

The second determination model uses one set of a mammography image and an ultrasound image that are determination targets as an input, and outputs a result (prediction result) of determining whether or not the first region of interest of the breast included in the mammography image and the second region of interest of the breast included in the ultrasound image are identical to each other on the basis of the training result. That is, by the second determination model, it is determined whether or not the first region of interest of the breast included in the radiation image and the second region of interest of the breast included in the ultrasound image are identical to each other.

The second determination model may output the result of determining being identical or being not identical, or may output the result of determining what percentage the ratio of match between the first region of interest of the breast included in the mammography image and the second region of interest of the breast included in the ultrasound image is.

The display control unit 33 displays various kinds of information on the monitor 34 under the control of the apparatus control unit 36. For example, the display control unit 33 performs predetermined processing on the ultrasound image held in the image memory 32, and displays the processed ultrasound image on the monitor 34. Further, the display control unit 33 displays the mammography image and the ultrasound image side by side on the monitor 34 or display the result of determination by the identity determination unit 46 on the monitor 34.

The apparatus control unit 36 controls each unit of the apparatus main body 3 on the basis of a program stored in advance and an instruction or the like of the user input from the input device 37. More specifically, the apparatus control unit 36 controls the display control unit 33 such that the ultrasound image is displayed on the monitor 34. The apparatus control unit 36 controls the region-of-interest processing unit 35 such that whether or not the region of interest of the breast included in the mammography image and the region of interest of the breast included in the ultrasound image are identical to each other is determined.

The image generation unit 31, the display control unit 33, the region-of-interest processing unit 35, and the apparatus control unit 36 constitute a processor 39 for the ultrasound diagnostic apparatus 20.

The monitor 34 displays various kinds of information under the control of the display control unit 33. The monitor 34 displays the mammography image, the ultrasound image, the result of the identity determination, and the like. Examples of the monitor 34 include a display device such as a liquid crystal display (LCD), and an organic electroluminescence (EL) display.

The input device 37 receives various instructions input from the user, and includes various buttons including a determination start button and a freeze button, and a touch panel or the like through which various instructions are input by the user performing a touch operation.

Figure 6:
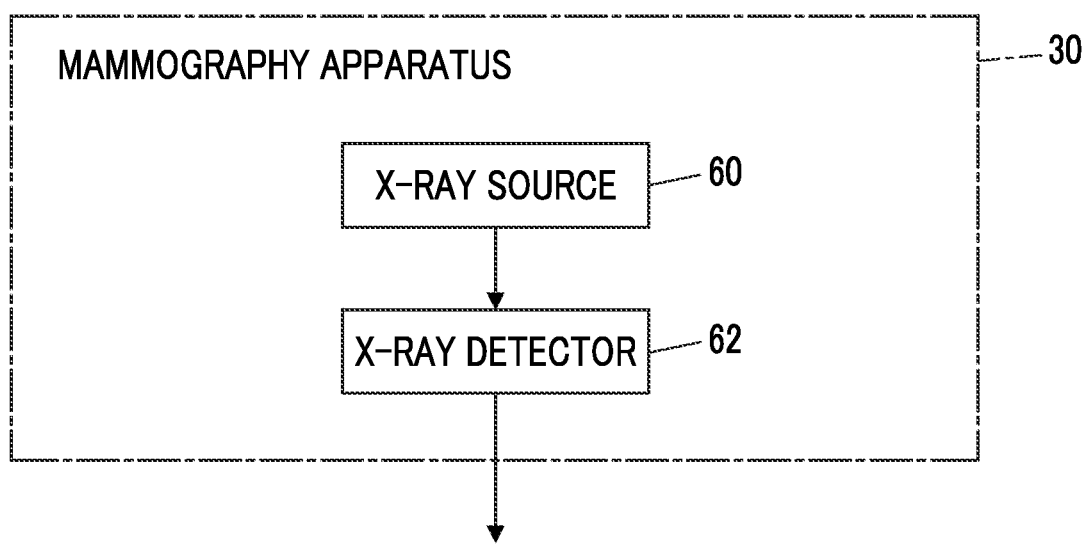
FIG. 6 is a block diagram of an embodiment illustrating a configuration of a mammography apparatus.

Next, FIG. 6 is a block diagram of an embodiment illustrating a configuration of the mammography apparatus. The mammography apparatus 30 illustrated in FIG. 6 includes an X-ray source 60 and an X-ray detector 62. In the mammography examination, the breast of the subject in an upright state is pressed by the compression plate, and the breast pressed by the compression plate is irradiated with the X-rays from the X-ray source 60. Then, the X-rays that have passed through the breast are detected by the X-ray detector 62, and the mammography image of the breast is generated from the detection signal detected by the X-ray detector 62.

In the mammography examination, for example, mammography images (R_MLO image and R_CC image) in a mediolateral-oblique (MLO) direction and a cranio-caudal (CC) direction of the right breast of the subject are generated. Similarly, mammography images (L_MLO image and L_CC image) in the MLO direction and the CC direction of the left breast of the subject are generated. That is, the R_MLO image, the R_CC image, the L_MLO image, and the L_CC image are generated.

The first region of interest of the breast included in the mammography image is specified by a first region-of-interest specifying unit. The first region-of-interest specifying unit has a function of extracting the first region of interest from the mammography image, and is computer-aided-detection (CAD) performed in the mammography apparatus 30, a computer associated with the mammography apparatus 30, a remote computer to be described later, or the like. The first region-of-interest specifying unit has a third determination model, and specifies the first region of interest of the breast of the subject included in the mammography image using the third determination model.

The third determination model is a trained model that has learned, using learning mammography images of the breast of any subject as third teacher data, a relationship between the learning mammography image and a region of interest of the breast included in the learning mammography image, for a plurality of pieces of the third teacher data.

The third determination model uses a mammography image that is a determination target as an input, and outputs a result (prediction result) of determining the first region of interest of the breast included in the mammography image on the basis of the training result. That is, the first region of interest of the breast included in the mammography image is specified by the third determination model.

The third determination model may learn normal data of the breast (data with no region of interest) as the third teacher data, and may output a determination result indicating being abnormal, that is, there is a first region of interest in a case where abnormal data (data with a region of interest) is input. Alternatively, the third determination model may learn abnormal data of the breast as the third teacher data, and may output a determination result indicating being normal, that is, there is no first region of interest in a case where normal data is input. The determination result may be output together with the coordinates and position of the extracted first region of interest.

It is not essential that the first region-of-interest specifying unit has the third determination model, and may specify the first region of interest of the breast included in the mammography image on the basis of an instruction to enclose the first region of interest of the breast with a rectangular frame line, which is input from the user, for example. Further, an image analysis unit that analyzes the mammography image may be provided, and the first region-of-interest specifying unit may specify the first region of interest of the breast included in the mammography image on the basis of an analysis result of the mammography image by the image analysis unit.

The information on the first region of interest included in the mammography image is supplied from the mammography apparatus to the ultrasound diagnostic apparatus 20 via the network 40 directly or picture archiving and communication systems (PACS) connected on the network 40. Alternatively, also in the ultrasound diagnostic apparatus 20, the first region of interest of the breast included in the mammography image can be specified on the basis of the instruction to enclose the first region of interest of the breast with a rectangular frame line, which is input from the user.

Figure 7:
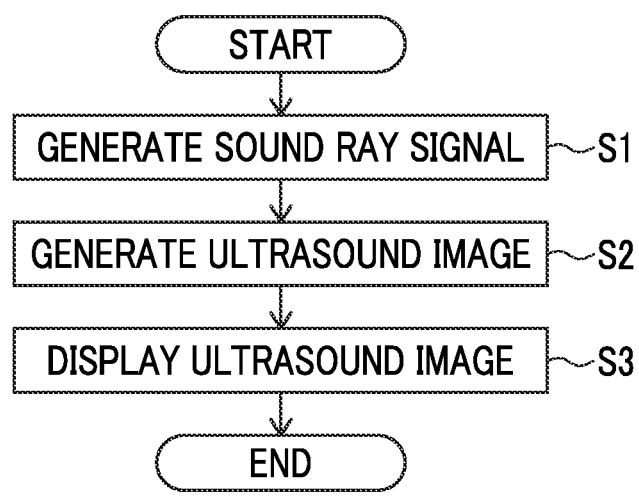
FIG. 7 is a flowchart of an embodiment illustrating an operation of an ultrasound system in a case of capturing an ultrasound image.

Next, the operation of the ultrasound system in a case where the ultrasound image is captured will be described with reference to the flowchart of FIG. 7.

First, in a state where the ultrasound probe 1 is in contact with the epidermis of the breast of the subject, under the control of the apparatus control unit 36, the transmission of the ultrasonic waves is started by the transmission and reception circuit 14, and the sound ray signal is generated (Step S1).

That is, the ultrasound beams are transmitted to the breast from a plurality of transducers of the transducer array 11 according to the drive signals from the pulser 51.

Ultrasound echoes from the breast based on the ultrasound beams transmitted from the pulser 51 are received by each transducer of the transducer array 11, and the reception signal as an analog signal is output from each transducer of the transducer array 11, which has received the ultrasound echo.

The reception signal as the analog signal output from each transducer of the transducer array 11 is amplified by the amplification unit 52, and is subjected to AD conversion by the AD conversion unit 53, and thereby the reception data is acquired.

By performing the reception focusing processing on the reception data by the beam former 54, the sound ray signal is generated.

Next, under the control of the apparatus control unit 36, the ultrasound image (ultrasound image signal) of the breast is generated by the image generation unit 31 on the basis of the sound ray signal generated by the beam former 54 of the transmission and reception circuit 14 (Step S2).

That is, the sound ray signal generated by the beam former 54 is subjected to various kinds of signal processing by the signal processing unit 16, and the image information data representing tomographic image information regarding tissues inside the subject is generated.

The image information data generated by the signal processing unit 16 is raster-converted by the DSC 18, and is further subjected to various kinds of image processing by the image processing unit 17, and thus the ultrasound image (ultrasound image signal) is generated.

The ultrasound image generated by the image processing unit 17 is held in the image memory 32.

Next, under the control of the apparatus control unit 36, predetermined processing is performed on the ultrasound image held in the image memory 32 by the display control unit 33, and the processed ultrasound image is displayed on the monitor 34 (Step S3).

Figure 8:
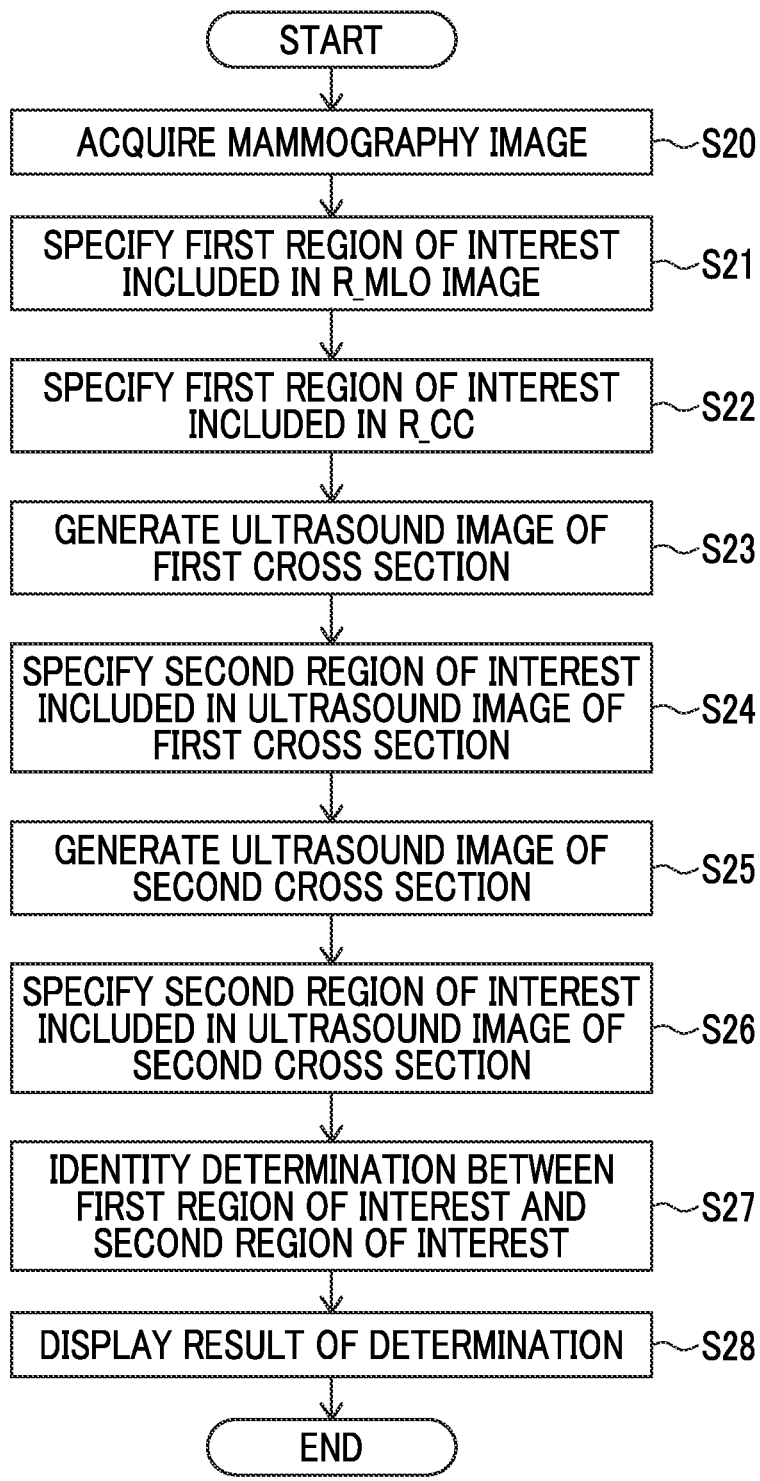
FIG. 8 is a flowchart of an embodiment illustrating an operation of an ultrasound system in a case of performing identity determination of a region of interest of a right breast.

Next, the operation of the ultrasound system in a case of performing identity determination of the region of interest of the right breast will be described with reference to the flowchart of FIG. 8.

First, in the ultrasound diagnostic apparatus 20, in response to the instruction from the user, the mammography image and the information on the first region of interest are acquired (Step S20) from the mammography apparatus 30 via the network 40 or preferably via the PACS on the network 40 by the apparatus control unit 36. In the present embodiment, in the ultrasound diagnostic apparatus 20, four mammography images consisting of the R_MLO image, the R_CC image, the L_MLO image, and the L_CC image are acquired from the mammography apparatus 30.

Figure 9:
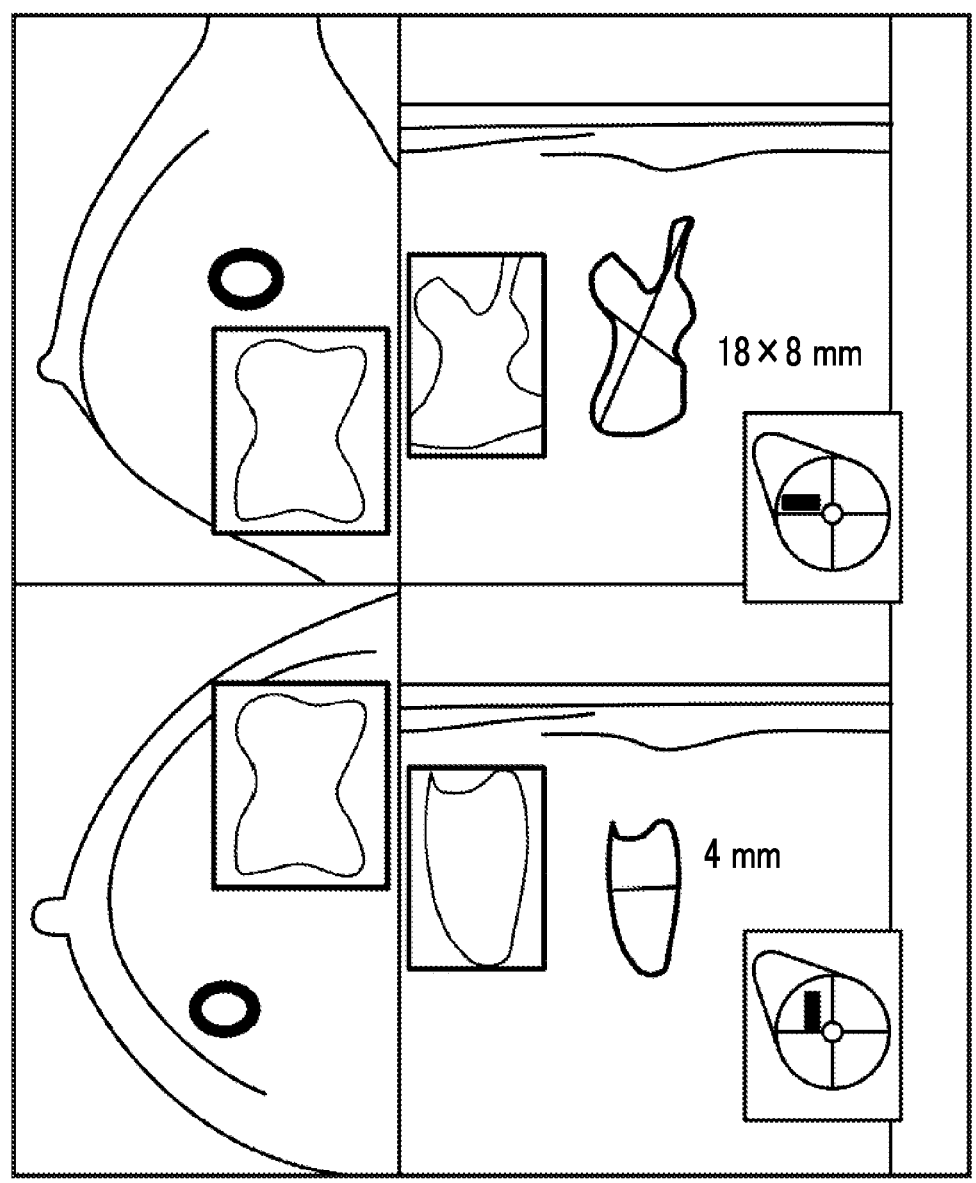
FIG. 9 is a conceptual diagram of an embodiment illustrating a display screen of a monitor.

For example, as illustrated in FIG. 9, the R_MLO image is displayed on an upper left display region on the display screen of the monitor 34 by the display control unit 33.

The first region of interest of the right breast included in the R_MLO image is enlarged to be displayed in a window region in a lower right portion of the upper left display region on the basis of the information on the first region of interest of the R_MLO image by the display control unit 33.

Similarly, for example, as illustrated in FIG. 9, the R_CC image is displayed on a lower left display region on the display screen of the monitor 34 by the display control unit 33.

The first region of interest of the right breast included in the R_CC image is enlarged to be displayed in a window region in an upper right portion of the lower left display region on the basis of the information on the first region of interest of the R_CC image by the display control unit 33.

As illustrated in FIG. 9, the first region of interest of the right breast included in each of the R_MLO image displayed on the upper left display region and the R_CC image displayed on the lower left display region is displayed surrounded by a circle frame.

Next, for example, the ultrasound image of a first cross section including the second region of interest of the right breast of the subject in a supine state, for example, the ultrasound image in a cross section in a lateral direction (left and right direction) with respect to the subject in a supine state is generated (Step S23) by the image generation unit, and the ultrasound image of the first cross section is displayed on an upper right display region on the display screen of the monitor 34 by the display control unit 33.

Next, the second region of interest of the right breast included in the ultrasound image of the first cross section is specified (Step S24) using the first determination model by the second region-of-interest specifying unit 44, and the second region of interest of the right breast included in the ultrasound image of the first cross section is enlarged to be displayed in a window region in the left center portion of the upper right display region by the display control unit 33.

As illustrated in FIG. 9, a schematic diagram of the right breast indicating the cross section position corresponding to the ultrasound image of the first cross section and the orientation of the ultrasound probe 1 is displayed on the lower right portion of the upper right display region. Further, in the second region of interest of the right breast included in the ultrasound image of the first cross section displayed in the upper right display region, for example, straight lines indicating a first diameter and a second diameter orthogonal to the first diameter and distances thereof are displayed.

Next, similarly, the ultrasound image of a second cross section including the second region of interest of the right breast of the subject in a supine state, for example, the ultrasound image in a cross section in a vertical direction (up and down direction) with respect to the subject in a supine state is generated (Step S25) by the image generation unit, and the ultrasound image of the second cross section is displayed on a lower right display region on the display screen of the monitor 34 by the display control unit 33.

As the ultrasound probe 1, for example, various ultrasound probes such as a 1D probe in which transducer arrays are arranged in a one-dimensional manner, a 2D probe in which transducer arrays are arranged in a two-dimensional manner, or a 1.5D probe are used. As the method of acquiring the ultrasound images of the first cross section and the second cross section, for example, there is a method of performing imaging by rotating the ultrasound probe 1 by 90°. As another acquisition method, acquisition may be performed by using the ultrasound probe that has transducer arrays arranged in a two-dimensional manner and can perform imaging without being rotated.

Next, the second region of interest of the right breast included in the ultrasound image of the second cross section is specified (Step S26) using the first determination model by the second region-of-interest specifying unit 44, and the second region of interest of the right breast included in the ultrasound image of the second cross section is enlarged to be displayed in a window region in the left center portion of the lower right display region by the display control unit 33.

As illustrated in FIG. 9, a schematic diagram of the right breast indicating the cross section position corresponding to the ultrasound image of the second cross section and the orientation of the ultrasound probe 1 is displayed on the lower right portion of the lower right display region. Further, in the second region of interest of the right breast included in the ultrasound image of the second cross section displayed in the lower right display region, for example, a straight line indicating a third diameter orthogonal to the first diameter and the second diameter and a distance thereof are displayed.

A determination start button is pressed by the user. In response, the identity determination unit 46 determines whether or not the first region of interest of the right breast included in the R_CC image specified on the basis of the information on the first region of interest of the R_CC image acquired from the outside and the second region of interest of the right breast included in the ultrasound image of the first cross section are identical to each other by using the second determination model (Step S27).

Then, the result of determination by the identity determination unit 46 is displayed on the monitor 34 by the display control unit 33 (Step S28). For example, as the result of determination by the identity determination unit 46, a result of determination such as "matched!" is displayed. The user can check whether or not the second region of interest of the right breast included in the ultrasound image of the first cross section is identical to the first region of interest of the right breast included in the R_CC image by watching the determination result displayed on the monitor 34, and can perform the diagnosis on the second region of interest of the right breast included in the ultrasound image of the first cross section.

In this manner, the ultrasound system can specify the second region of interest of the breast included in the ultrasound image, and automatically determine whether or not the first region of interest of the breast included in the mammography image is identical to the second region of interest. Therefore, the user does not confuse the first region of interest of the breast included in the mammography image and the second region of interest of the breast included in the ultrasound image, and the user can be prevented from performing a biopsy on the wrong region of interest of the breast.

The ultrasound images of the first cross section and the second cross section may be videos of the first cross section and the second cross section. In this case, the second region-of-interest specifying unit 44 uses the video as an input, and specifies the second region of interest of the breast included in the video using the first determination model.

While the second region of interest of the right breast included in the ultrasound image of the second cross section is specified and is enlarged to be displayed, the ultrasound image of the first cross section and the second region of interest of the right breast thereof displayed in an enlarged manner may not be displayed. In other words, after the second region of interest of the right breast included in the ultrasound image of the second cross section is specified, the ultrasound images of the first cross section and the second cross section may be simultaneously displayed on the monitor 34, and the second region of interest of the right breast of each of the ultrasound images may be enlarged to be displayed on the monitor 34.

An example of performing the identity determination between the first region of interest of the right breast included in the R_CC image and the second region of interest of the right breast included in the ultrasound image of the first cross section has been described, but the present invention is not limited thereto, and the identity determination unit 46 may perform determination on the basis of the radiation image in one direction, the radiation image including the first region of interest or the radiation images in two different directions, the radiation images including the first region of interest. Similarly, the identity determination unit 46 may perform determination on the basis of the ultrasound image of one cross section, the ultrasound image including the second region of interest or the ultrasound images of two cross sections orthogonal to each other, the ultrasound images including the second region of interest. The same applies to the left breast.

The identity determination unit 46 can perform the identity determination using at least one mammography image and one ultrasound image of the same breast, and as in the present embodiment, the R_CC image and the ultrasound image of the first cross section preferable because the images have the same observation direction. On the other hand, by performing the identity determination using the mammography images in two directions and the ultrasound images of two cross sections, it is possible to improve the accuracy of the identity determination by the identity determination unit 46. Further, the user can easily predict the stereoscopic images of the first region of interest and the second region of interest by watching the mammography images in two directions and the ultrasound images of two cross sections, and as a result, the user can easily predict the result of the identity determination.

Further, the identity determination unit 46 may perform determination on the basis of volume data consisting of ultrasound images of a plurality of cross sections different from each other, the ultrasound images including the second region of interest of the breast, or the three-dimensional image reconstructed using the volume data. As a result, it is possible to further improve the accuracy of the identity determination by the identity determination unit 46.

In the present embodiment, the identity determination unit 46 starts the determination on the basis of a determination start instruction input from the user, such as pressing the determination start button by the user, but the present invention is not limited thereto. For example, the identity determination unit 46 may start the determination on the basis of an instruction of a freeze operation for the ultrasound image input from the user, which does not relate to the determination start instruction, or may start the determination after the ultrasound image is generated on the basis of the instruction of the freeze operation for the ultrasound image input from the user, on the basis of an instruction to enclose the second region of interest of the breast with a rectangular frame line, which is input from the user.

In a case where it is specified that a plurality of first regions of interest are included in the radiation image or a plurality of second regions of interest are included in the ultrasound image, that is, in a case where there is a possibility of multiple lesions, the identity determination unit 46 may automatically start the determination. In this case, the identity determination of one region of interest of the breast, which is selected on the basis of an instruction to select the region of interest of the breast from the plurality of regions of interest, which is input from the user, may be performed.

In a case where there is a possibility of multiple lesions, since the first region of interest of the breast specified in the mammography image and the second region of interest of the breast specified in the ultrasound image are confused in a case of performing a biopsy of the breast while watching the ultrasound image, there have been cases in actual medical fields in which the biopsy is performed on the wrong region of interest of the breast. On the other hand, as described above, in a case where a plurality of regions of interest are specified, in a case where a function of performing the identity determination is provided, it is possible to reduce the confusion of the region of interest in a case of performing a biopsy and shorten the biopsy time.

The ultrasound diagnostic apparatus 20 may acquire the mammography image from the remote computer instead of directly acquiring the mammography image from the mammography apparatus 30.

Figure 10:
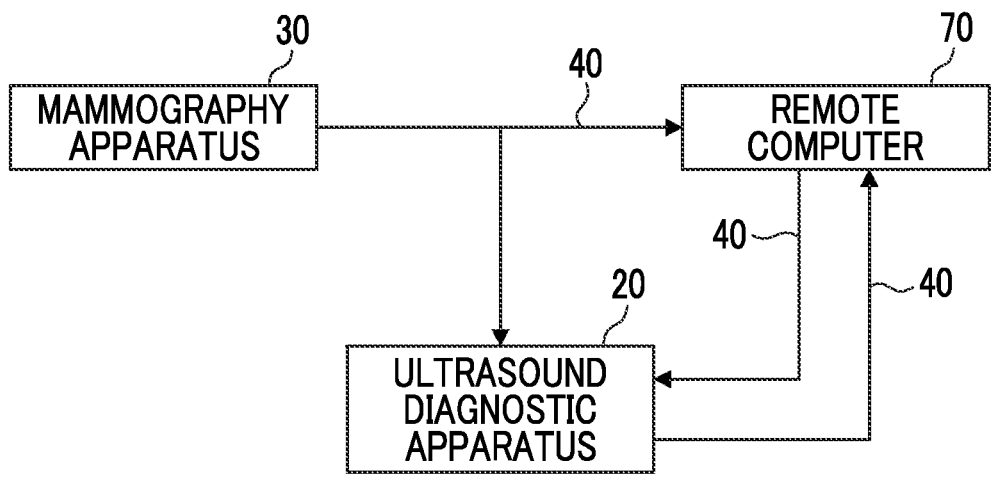
FIG. 10 is a block diagram of an embodiment illustrating a configuration in a case where an ultrasound diagnostic apparatus acquires a mammography image from a remote computer.

FIG. 10 is a block diagram of an embodiment illustrating a configuration in a case where the ultrasound diagnostic apparatus acquires the mammography image from the remote computer. As illustrated in FIG. 10, the mammography apparatus 30 is connected to each of the ultrasound diagnostic apparatus 20 and a remote computer 70 via the network 40. Further, the ultrasound diagnostic apparatus 20 and the remote computer 70 are connected to each other via the network 40, and thereby data can be bidirectionally delivered.

Here, the remote computer 70 is a workstation or a PACS connected to the ultrasound diagnostic apparatus 20 and the mammography apparatus 30 via the network 40.

In the configuration illustrated in FIG. 10, the remote computer 70 receives the mammography image transmitted from the mammography apparatus 30 via the network 40 and the ultrasound image transmitted from the ultrasound diagnostic apparatus 20 via the network 40, and stores and manages the mammography image and the ultrasound image. The ultrasound diagnostic apparatus 20 can directly acquire the mammography image from the mammography apparatus 30 via the network 40 or acquire the mammography image from the remote computer 70 via the network 40.

The identity determination may be performed in the ultrasound diagnostic apparatus 20, or the identity determination may be performed in the remote computer 70. In a case where the identity determination is performed in the ultrasound diagnostic apparatus 20, the remote computer 70 is not required, and the ultrasound diagnostic apparatus 20 includes all the constituents illustrated in FIG. 1, for example, the ultrasound probe 1, the image generation unit, the region-of-interest processing unit 35, and the like. On the other hand, in a case where the identity determination is performed in the remote computer 70, the remote computer 70 includes the identity determination unit, and the ultrasound diagnostic apparatus 20 includes the constituents other than the identity determination unit, for example, the ultrasound probe 1, the image generation unit, the second region-of-interest specifying unit 44, and the like. The second region-of-interest specifying unit 44 may be included in the ultrasound diagnostic apparatus 20 or may be included in the remote computer 70.

Figure 11:
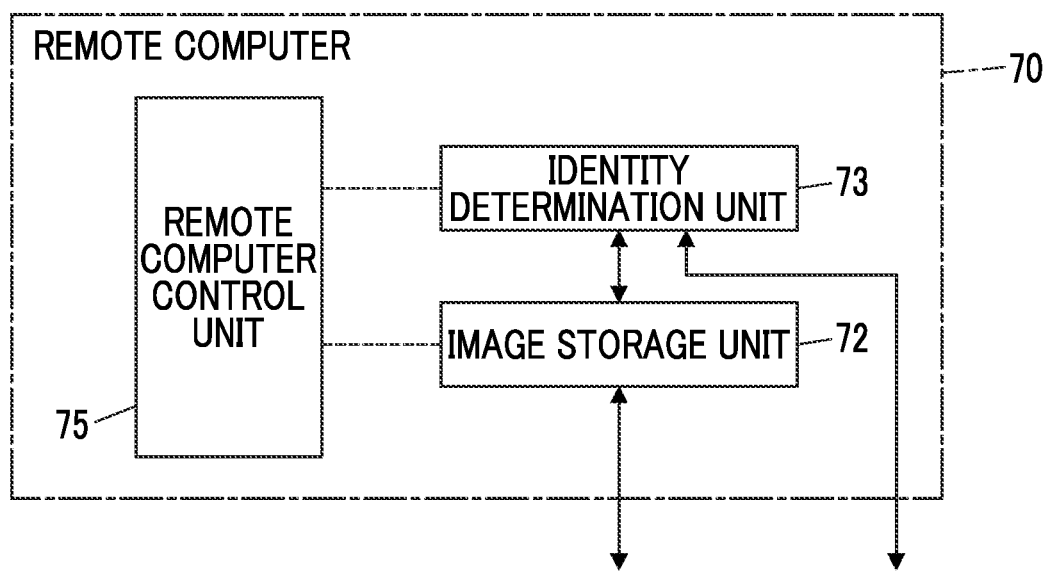
FIG. 11 is a block diagram of an embodiment illustrating a configuration of a remote computer.

FIG. 11 is a block diagram of an embodiment illustrating a configuration of the remote computer. The remote computer 70 illustrated in FIG. 11 includes an identity determination unit 73, an image storage unit 72, and a remote computer control unit 75. The identity determination unit 73 is bidirectionally connected to the image storage unit 72. The remote computer control unit 75 is connected to the identity determination unit 73 and the image storage unit 72.

The remote computer 70 may include a region-of-interest processing unit similar to the region-of-interest processing unit 35 of the ultrasound diagnostic apparatus 20, in addition to the identity determination unit 73. That is, the remote computer 70 may include a second region-of-interest specifying unit similar to the second region-of-interest specifying unit 44.

The identity determination unit 73 is the same as the identity determination unit 46 of the apparatus main body 3 of the ultrasound diagnostic apparatus 20, but is operated under the control of the remote computer control unit 75.

The image storage unit 72 stores medical images such as mammography images and ultrasound images. For example, the image storage unit 72 may be a storage device that stores medical images in the remote computer 70. Alternatively, instead of the image storage unit 72, an image storage unit on the PACS connected on the network 40 can be used.

The remote computer control unit 75 controls each unit of the remote computer 70 on the basis of a program and the like stored in advance. More specifically, the remote computer control unit 75 controls the identity determination unit 73 such that the identity determination is performed. Further, the remote computer control unit 75 controls the image storage unit 72 such that the medical images such as the mammography images and the ultrasound images are stored.

In a case where the identity determination is performed in the remote computer 70, the mammography image and the ultrasound image that are determination targets are acquired from the medical images that have been stored in the image storage unit 72 by the identity determination unit 73, for example. The operation of the identity determination unit 73 is similar to the operation in a case where the identity determination unit 46 performs the identity determination in the ultrasound diagnostic apparatus 20. After the identity determination is performed in the remote computer 70, the result of the identity determination is transmitted from the remote computer 70 to the ultrasound diagnostic apparatus 20.

Then, in the ultrasound diagnostic apparatus 20, the result of the identity determination is displayed on the monitor 34 by the display control unit 33.

The identity determination is performed in the remote computer 70, the result of the identity determination is transmitted to the ultrasound diagnostic apparatus 20, and the result of the determination is displayed on the monitor 34 of the ultrasound diagnostic apparatus 20 by the display control unit of the ultrasound diagnostic apparatus 20. However, the present invention is not limited thereto. For example, in a case where the remote computer 70 is a workstation, the identity determination may be performed in the workstation, and the result of the identity determination may be displayed on a monitor of the workstation by a display control unit of the workstation. Further, in a case where the workstation includes a client connected via the network 40, the identity determination may be performed in the workstation, the result of the identity determination may be transmitted from the workstation to the client, and the result of the identity determination may be displayed on a monitor of the client by a display control unit of the client. Further, in a case where the remote computer 70 is the PACS, the identity determination may be performed in the PACS, and the result of the identity determination may be displayed on a monitor of the PACS by a display control unit of the PACS. The identity determination may be performed in the ultrasound diagnostic apparatus 20, and the result of the determination may be displayed on the monitor 34 of the ultrasound diagnostic apparatus 20 by the display control unit of the ultrasound diagnostic apparatus 20, or the result of the identity determination may be transmitted to the remote computer 70, and the result of the determination may be displayed on the monitor 34 of the remote computer 70 by the display control unit of the remote computer 70.

In a case where the remote computer 70 is a workstation, the radiation image and the ultrasound image of the same subject may be displayed side by side on the monitor of the workstation by the display control unit of the workstation. Further, in a case where the workstation includes a client connected via the network 40, the radiation image and the ultrasound image of the same subject may be transmitted from the workstation to the client, and the radiation image and the ultrasound image of the same subject may be displayed side by side on the monitor of the client by the display control unit of the client. In a case where the remote computer 70 is the PACS, the radiation image and the ultrasound image of the same subject may be displayed side by side on the monitor of the PACS by the display control unit of the PACS. In this manner, even in a case where the identity determination is performed in either the ultrasound diagnostic apparatus 20 or the remote computer 70, in at least one of the ultrasound diagnostic apparatus 20 or the remote computer 70, the radiation image and the ultrasound image of the same subject can be displayed side by side on the monitor 34 by the display control unit.

In the present invention, radiation images generated by various radiological diagnostic apparatuses including CT devices and MRI devices can be used without the limitation on the mammography images generated by the mammography apparatus 30.

The present invention is not limited to a stationary ultrasound system, and can be similarly applied to a portable ultrasound system in which an apparatus main body is realized by a laptop terminal device, and a handheld ultrasound system in which an apparatus main body is realized by a handheld terminal device such as a smartphone or a tablet personal computer (PC).

In the device of the present invention, the hardware configurations of the processing units executing various kinds of processing such as the transmission and reception circuit 14, the signal processing unit 16, the image generation unit 31, the display control unit 33, the region-of-interest processing unit 35, and the apparatus control unit 36 may be dedicated hardware, or may be various processors or computers that execute programs. The hardware configuration of the image memory 32, the image storage unit 72, and the like may be dedicated hardware, or may be a memory such as a semiconductor memory and a storage device such as a hard disk drive (HDD) and a solid state drive (SSD).

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing a specific process such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor fulfilling the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: apparatus main body
11: transducer array
14: transmission and reception circuit
16: signal processing unit
17: image processing unit
18: DSC
20: ultrasound diagnostic apparatus
30: mammography apparatus
32: image memory
33: display control unit
34: monitor
35: region-of-interest processing unit
36: apparatus control unit
37: input device
39: processor
40: network
44: second region-of-interest specifying unit
46, 73: identity determination unit
51: pulser
52: amplification unit
53: AD conversion unit
54: beam former
60: X-ray source
62: X-ray detector
70: remote computer
72: image storage unit
75: remote computer control unit

What is claimed is:
1. An ultrasound system comprising:
an ultrasound probe; and
a first processor,
wherein the first processor
generates, from a reception signal obtained by performing transmission and reception of an ultrasound beam with respect to a breast of a subject by using the ultrasound probe, an ultrasound image including a second region of interest of the breast of the subject corresponding to a first region of interest of the breast of the subject included in a radiation image,
specifies the second region of interest included in the ultrasound image, and
determines whether or not the first region of interest included in the radiation image and the second region of interest are identical to each other,
wherein the first processor has a first determination model that has learned, using learning ultrasound images of the breast of the subject as first teacher data, a relationship between the learning ultrasound image and a region of interest included in the learning ultrasound image for a plurality of pieces of the first teacher data, and
the first determination model uses the ultrasound image as an input, and specifies the second region of interest included in the ultrasound image.

2. The ultrasound system according to claim 1, further comprising:
an ultrasound diagnostic apparatus,
wherein the ultrasound diagnostic apparatus includes the ultrasound probe, and the first processor.

3. The ultrasound system according to claim 1, further comprising:
an ultrasound diagnostic apparatus; and
a remote computer connected to the ultrasound diagnostic apparatus via a network,
wherein the ultrasound diagnostic apparatus includes the ultrasound probe and a second processor,
the second processor generates, from a reception signal obtained by performing transmission and reception of an ultrasound beam with respect to a breast of a subject by using the ultrasound probe, an ultrasound image including a second region of interest of the breast of the subject corresponding to a first region of interest of the breast of the subject included in a radiation image, and
the remote computer determines whether or not the first region of interest included in the radiation image and the second region of interest are identical to each other.

4. The ultrasound system according to claim 2,
wherein the ultrasound diagnostic apparatus includes a monitor and a third processor, and the third processor displays the radiation image and the ultrasound image side by side on the monitor.

5. The ultrasound system according to claim 3,
wherein the remote computer is a workstation, and includes a monitor and a third processor, and
the third processor displays the radiation image and the ultrasound image side by side on the monitor.

6. The ultrasound system according to claim 3,
wherein the remote computer is a workstation,
the workstation includes a client connected via the network,
the client includes a monitor and a third processor, and
the third processor displays the radiation image and the ultrasound image side by side on the monitor.

7. The ultrasound system according to claim 3,
wherein the remote computer is a picture archiving and communication system,
the picture archiving and communication system includes a monitor and a third processor, and
the third processor displays the radiation image and the ultrasound image side by side on the monitor.

8. The ultrasound system according to claim 4,
wherein the third processor enlarges and displays each of the first region of interest included in the radiation image and the second region of interest included in the ultrasound image on the monitor.

9. The ultrasound system according to claim 4,
wherein the third processor displays a result of determination by the first processor on the monitor.

10. The ultrasound system according to claim 1,
wherein the first processor performs determination on the basis of a radiation image in one direction, the radiation image including the first region of interest, or radiation images in two directions different from each other, the radiation images including the first region of interest.

11. The ultrasound system according to claim 1,
wherein the first processor performs determination on the basis of an ultrasound image of one cross section, the ultrasound image including the second region of interest, or ultrasound images of two cross sections orthogonal to each other, the ultrasound images including the second region of interest.

12. The ultrasound system according to claim 1,
wherein the first processor performs determination on the basis of volume data consisting of ultrasound images of a plurality of cross sections different from each other, the ultrasound images including the second region of interest, or a three-dimensional image reconstructed using the volume data.

13. The ultrasound system according to claim 1,
wherein the first processor specifies the second region of interest included in the ultrasound image on the basis of an instruction to designate the second region of interest, input from the user.

14. The ultrasound system according to claim 1,
wherein the ultrasound image is a video, and
the first determination model uses the video as an input, and specifies the second region of interest included in the video.

15. The ultrasound system according to claim 1,
wherein the first processor has a second determination model that has learned, using learning radiation images including a region of interest of the breast of the subject and the learning ultrasound images including the same region of interest of the breast of the subject as the region of interest included in the learning radiation image as one set of second teacher data, a relationship between the learning radiation image and the learning ultrasound image, and whether or not the region of interest included in the learning radiation image and the region of interest included in the learning ultrasound image are identical to each other, for a plurality of pieces of the second teacher data, and
the second determination model uses one set of the radiation image and the ultrasound image as an input, and outputs a result of determination on whether or not the first region of interest included in the radiation image and the second region of interest included in the ultrasound image are identical to each other.

16. The ultrasound system according to claim 1,
wherein the first processor starts determination on the basis of a determination start instruction input from the user.

17. The ultrasound system according to claim 1,
wherein the first processor starts determination on the basis of an instruction of a freeze operation for the ultrasound image input from the user.

18. The ultrasound system according to claim 17,
wherein the first processor starts determination on the basis of an instruction to designate the second region of interest input from the user after the ultrasound image is generated on the basis of the instruction of the freeze operation for the ultrasound image input from the user.

19. The ultrasound system according to claim 1,
wherein the first processor starts determination in a case where it is specified that a plurality of the first regions of interest are included in the radiation image or a plurality of the second regions of interest are included in the ultrasound image.

20. The ultrasound system according to claim 1,
wherein the first processor specifies the second region of interest included in the ultrasound image on the basis of information on the first region of interest in the radiation image acquired from outside.

21. A control method of an ultrasound system, the control method comprising:
generating, from a reception signal obtained by performing transmission and reception of an ultrasound beam with respect to a breast of a subject by using an ultrasound probe, an ultrasound image including a second region of interest of the breast of the subject corresponding to a first region of interest of the breast of the subject included in a radiation image;

specifying the second region of interest included in the ultrasound image; and determining whether or not the first region of interest included in the radiation image and the second region of interest are identical to each other, wherein the second region of interest in the ultrasound image is specified by inputting the ultrasound image to a first determination model that has learned, using learning ultrasound images of the breast of the subject as first teacher data, a relationship between the learning ultrasound image and a region of interest included in the learning ultrasound image for a plurality of pieces of the first teacher data.

* * * * *